US007052589B1

(12) United States Patent
Vigh

(10) Patent No.: US 7,052,589 B1
(45) Date of Patent: May 30, 2006

(54) METHOD FOR ELECTROPHORETIC SEPARATIONS USING DYNAMICALLY GENERATED OPPOSITE MOBILITIES

(75) Inventor: Gyula Vigh, Magnolia, TX (US)

(73) Assignee: The Texas A&M University System, College Station, TX (US)

( * ) Notice: Subject to any disclaimer, the term of this patent is extended or adjusted under 35 U.S.C. 154(b) by 322 days.

(21) Appl. No.: 10/100,549

(22) Filed: Mar. 18, 2002

Related U.S. Application Data

(60) Provisional application No. 60/277,126, filed on Mar. 19, 2001.

(51) Int. Cl.
*G01N 27/447* (2006.01)
(52) U.S. Cl. .................................. 204/451; 204/454
(58) Field of Classification Search ................ 204/548, 204/459, 462, 610, 613, 644, 454, 601, 451
See application file for complete search history.

(56) References Cited

OTHER PUBLICATIONS

Wan et al, J. Chromatog. A, 704, pp. 179-193 (1995).*
Bauer et al. "Sodium Chloride in Preparative Free-Flow Cell Electrophoresis: Recent Developments" Electrophoresis, vol. 17, pp. 526-528, 1996.
Bauer et al. "Interval Carrier Free Electrophoresis For High Resolution Protein Purification" J Dispersion Science and Technology, vol. 19, pp. 937-950, 1998.
Bier et al. "A New Buffering System and Its Use in Electrophoresis and Isoelectric Focusing" Electrophoresis, vol. 14, pp. 1011-1018, 1993.
Bondy et al. "Sodium Chloride in Separation Medium Enhances Cell Compatibility of Free Flow Electrophoresis" Electrophoresis, vol. 16, pp. 92-97, 1995.
Burggraf et al. "Free Flow-Isoelectric Focusing of Human Cellular Lysates as Sample Preparation for Protein Analysis" Electrophoresis, vol. 16, pp. 1010-1015, 1995.
Cai et al. "A Family of Single-Isomer Chiral Resolving Agents for Capillary Electrophoresis. 3. Heptakis(2,3-dimethyl-6-sulfato)-β-cyclodextrin" Analytical Chemistry, vol. 70, pp. 580-589, 1998.
Cai et al. "Capillary Electrophoretic Separation of Weak Base Enantiomers Using the Single-Isomer Heptakis-(2,3 Dimethyl-6-sulfacto)-β-Cyclodextrin as Resolving Agent and Methanol as Background Electrolyte Solvent" J. Pharm. Biomded. Anal., vol. 18, pp. 615-621, 1998.

(Continued)

*Primary Examiner*—Kaj K. Olsen
(74) *Attorney, Agent, or Firm*—Baker Botts L.L.P.

(57) ABSTRACT

Method and materials to carry out preparative-scale electrophoretic separations based on the principle of dynamically created non-co-directional effective electrophoretic mobilities are disclosed. The primary application areas of the method are in the separation, purification, enrichment, concentration or conditioning of both small and large molecular weight, weak and strong electrolyte compounds, such as pharmaceuticals, oligo- and polypeptides, proteins, oligonucleotides, etc. These objectives can be achieved based on the use of a secondary chemical equilibrium, alone or in combination with multiple protic and other secondary chemical equilibria. Though such electrophoretic operations could be achieved by other means, such as by conventional zone electrophoresis or isotachophoresis, the method disclosed here can provide greater separation power, simplicity and higher production rates.

18 Claims, 8 Drawing Sheets

OTHER PUBLICATIONS

Canut et al. "Separation of Plant Membranes by Electromigration Techniques" J. Chromatography B, vol. 722, pp. 121-139, 1999.

Chankvetadze, B. "Capillary Electrophoresis in Chiral Analysis" John Wiley & Sons, New York, Table of Contents Only, 1997.

Glukhovskiy et al., "Analytical- and Preparative-Scale Isoelectric Focusing Separation of Enantiomers" Analytical Chemistry vol. 71, pp. 3814-3820, 1999.

Glukhovskiy, et al. "Preparative-Scale Isoelectric Focusing Separation of Enantiomers Using a Multicompartment Electrolyzer with Isoelectric Membranes" Electrophoresis, vol. 21, pp. 762-766, 2000.

Guiochon, G, et al. "Fundamentals of Preparative and Non-linear Chromatography" Academic Press, New York, Table of Contents Only, 1994.

Hoffmann et al. "Separation and Purification of Methadone Enantiomers by Continuous- and Interval-Flow Electrophoresis" Analytical Chemistry, vol. 71, pp. 1840-1850, 1999.

Juza et al. "Simulated Moving-Bed Chromatography and Its Application to Chirotechnology" Trends in Biotech vol. 18, pp. 108-118, 2000.

Krivankova et al. "Continuous Free-Flow Electrophoresis" Electrophoresis, vol. 19, pp. 1064-1074, 1998.

Lanz, M. et al. "Enantiomeric Separation of methadone by Cyclodextrin-Based Capillary and Recycling Isotachophoresis" Electrophoresis, vol. 19, pp. 1081-1090, 1998.

Nath et al. "Separation of Enzymes From Microorganism Crude Extracts by Free-Flow Zone Electrophoresis" Biotechnology and Bioengineering, vol. 51, pp. 15-22, 1996.

Rhodes et al. PElectrohydrodynamic Effects in Continuous Flow Electrophoresis Applied and Theoretical Electrophoresis vol. 2, pp. 87-98, 1991.

Stalcup, A. et al. "Application of Classical Gel Electrophoresis to the Chiral Separation of Milligram Quantities of Terbutaline" Analytical Chemistry, vol. 70, pp. 144-148, 1998.

Taker et al. "Nonaqueous Capillary Electrophoretic Separation of Basic Enantiomers Using Heptakis(2,3-dimethyl-6-sulfato)-β-cyclodextrin" Electrophoresis vol. 20, pp. 2794-2798, 1999.

Glukhovskiy et al. "Use of Single-Isomer, Multiply-Charged Chiral Resolving Agents for the Continuous, Preparative-Scale Electrophoretic Separation of Enantiomers Based on the Principle of Equal-But-Opposite 6Analyte Mobilities," Electrophoresis vol. 21, pp. 2010-2015, 2000.

Vincent et al. "A Family of single-Isomer Chiral Resolving Agents for Capillary Electrophoresis. 1. Heptakis(2,3-diacetyl-6-sulfato)-β-cyclodextrin" Analytical Chemistry, vol. 69, pp. 4226-4233, 1997.

Vincent et al. "A Family of Single-Isomer Chiral Resolving Agents for Capillary Electrophoresis. 2. Hepta-6-sulfato-β-cyclodextrin" Analytical Chemistry vol. 69, pp. 4419-4428, 1997.

Vincent et al. "Nonaqueous Capillary electrophoretic Separation of Enantiomers Using the Single-Isomer Heptakis(2,3-diacetyl-6-sulfato)-β-cyclodextrin as Chiral Resolving Agent" J. Chromatography A, vol. 816, pp. 233-241, 1998.

Vincent et al. "Systematic Approach to Methods Development for the Capillary Electrophoretic Analysis of a Minor Enantiomer Using a Single-Isomer Sulfated Cyclodextrin. A Case Study of L-Carbidopa Analysis" J. Chromatography A, vol. 817, pp. 105-111, 1998.

Weber et al. "Optimized Continuous Flow Electrophoresis" Electrophoresis, vol. 17, pp. 1906-1910, 1996.

Weber et al. "Counterbalancing Hydrodynamic Sample Distortion Effects Increases Resolution of Free-Flow Zone Electrophoresis" Electrophoresis, vol. 19, pp. 1104-1109, 1998.

Weber et al. "Recent Developments in Preparative Free Flow Isoelectric Focusing" Electrophoresis, vol. 19, pp. 1649-1653, 1998.

Weber et al. "Interval Isotachophoresis for Purification and Isolation of Ionogenic Species" Electrophoresis, vol. 19, pp. 3090-3093, 1998.

Weber et al. "Stability of Continuous Flow Electrophoresis" Electrophoresis, vol. 19, pp. 3094-3095, 1998.

Weber et al. "Application of Binary Buffer Systems to Free Flow Cell Electrophoresis" Electrophoresis, vol. 21, pp. 325-328, 2000.

William et al., "The Use of Hydrodynamic Counterflow to Improve the Resolution and Detection of the Minor Component in the Capillary Electrophoretic Analysis of Enantiomers." Enantiomer vol. 1, pp. 183-191, 1996.

Williams et al. "Dry Look at the CHARM (Charged Resolving Agent Migrationl) Model of Enantiomer Separations by Capillary Electrophoresis", J. Chromatography A vol. 777, pp. 295-309, 1997.

Zhu et al. "A Family of Single-Isomer, Sulfated γ-Cyclodextrin Chiral Resolving Agents for Capillary Electrophoresis. 1. Octakis(2,3-diacetyl-6-sulfato)-γ-cyclodextrin" Analytical Chemistry, vol. 72, pp. 310-317, 2000.

* cited by examiner

METHOD FOR ELECTROPHORETIC SEPARATIONS USING DYNAMICALLY GENERATED OPPOSITE MOBILITIES

CROSS REFERENCE TO RELATED APPLICATION

This application claims priority to U.S. Provisional Application Ser. No. 60/277,126 filed Mar. 19, 2001, and entitled Method for Electrophoretic Separations Using Dynamically Generated Opposite Mobilites.

BACKGROUND OF THE INVENTION

1. Field of the Invention

This invention relates to preparative-scale separation of components by electrophoresis. More particularly, method and apparatus for altering the initial composition of a feed solution by electrophoretic separations using a resolving agent to dynamically alter the sign of the effective mobility of the band of one or more selected sample components in the feed solution is provided.

2. Description of Related Art

The ability to conduct preparative-scale chromatographic enantiomer separations has improved significantly during the last decade. Once the fundamentals of nonlinear chromatography became well understood and adequate hardware became readily available, many batch-wise nonlinear chromatographic separations were converted to continuous separations, using a simulated moving bed approach, to achieve higher productivities. [Juza, M. et al., *Trends in Biotech.* 2000, 18, 108–118] Mirroring these developments, as understanding of capillary electrophoretic enantiomer separations improved, preparative-scale electrophoretic enantiomer separations were attempted. The appearance of a new, continuous, free-flow electrophoretic units, such as the "Octopus," permitted exploration of the conversion of batch-type electrophoretic separations to continuous, preparative-scale separations that can alter the initial composition of the feed solution. These developments are more fully explained in a recent paper co-authored by the inventor ["Use of Single-Isomer, Multiply-Charged Chiral Resolving Agents for the Continuous, Preparative-Scale Electrophoretic Separation of Enantiomers Based on the Principle of Equal-But-Opposite Analyte Mobilities," *Electrophoresis* 2000, 21, 1019–1026], which is hereby incorporated by reference herein.

The Octopus unit is illustrated in FIG. 1 (Prior Art). There is a continuous, laminar flow of the separation medium, orthogonal to the electric field, through shallow, rectangular electrophoresis chamber 10 of the unit. The sample is continuously fed at inlet 12, above inlet ports 14 where the separation medium enters the unit, either at the center or at one of the sides of the chamber. The separated components, dissolved in the separation medium, are collected through sampling ports 16 as they leave the separation chamber. The sampling ports (normally including 96 ports) provide a lateral spatial resolution of about 1 mm per collection port across the 100 mm wide separation chamber. Recent studies indicated that the reproducibility and long-term stability of the separation patterns obtained in the Octopus unit were satisfactory.

The Octopus unit is well suited for preparative-scale, continuous isoelectric focusing separations because the well known isoelectric focusing mechanism successfully counters most of the flow-related band broadening mechanisms. The Octopus unit has been successfully used for the preparative-scale isoelectric focusing separation of the enantiomers of dansyl phenylalanine with 30 mM hydroxypropyl β-cyclodextrin as chiral resolving agent in binary Bier buffers. [P. Glukhovskiy et al., *Anal. Chem.*, 1999, 71, 3814–3820] The Octopus unit has also been used for the much more difficult, continuous free-flow and intermittent-flow electrophoretic separation of the enantiomers of methadone with non-charged hydroxypropyl β-cyclodextrin as the chiral resolving agent. [P. Hoffmann et al., *Anal. Chem.*, 1999, 71, 1840–1850] In both of these flow modes, the cationic methadone enantiomers were injected at the anodic side of the separation chamber (opposite to fraction collection ports 19–20), and were collected, partially separated, in fractions 52–96 (continuous flow mode) and fractions 72–96 (intermittent flow mode). This means that in the continuous flow mode the available separation distance was only twice as large (about 80 ports wide) as the band width of each enantiomer (about 44 ports wide) resulting in an alteration of the initial composition of the feed solution. The situation was a little better in the intermittent flow mode, where the available separation distance (about 80 ports wide) was four times as large as the band width of each enantiomer (about 20 ports wide) resulting, once again, in an alteration of the initial composition of the feed solution. Clearly, one would need a much larger separation distance (much wider separation chamber) if one wanted to completely eliminate the overlap of the enantiomer bands to not only alter the initial composition of the feed solution, but recover each enantiomer in pure form.

In general, the separation of two like-charged analyte ions of similar, but not identical effective mobilities (derived either from strong electrolytes or weak electrolytes) by electrophoresis typically requires the use of long migration distances and/or large applied electric potentials. While these requirements can be fulfilled relatively easily in capillary electrophoresis for analytical-scale separations, they are often difficult or impossible to meet in preparative-scale separation.

Hydrodynamic flows or electroosmotic flows have been utilized to shift the observed mobilities of at least one of the analytes to be separated, as described, e.g., in the paper by B. A. William and Gy. Vigh, "The Use of Hydrodynamic Counterflow to Improve The Resolution of the Minor Component in the Capillary Electrophoretic Analysis of Enantiomers." *Enantiomer* 1 (1996) 183. However, due to the frequently poor temporal stability of the electroosmotic flow, and the extra band broadening created by the laminar hydrodynamic flow, these approaches are not conducive to efficient preparative-scale separations. What is needed is a method for use in preparative-scale electrophoresis that can alter the initial composition of the feed solution over relatively short migration distances.

SUMMARY OF THE INVENTION

Figure 1:
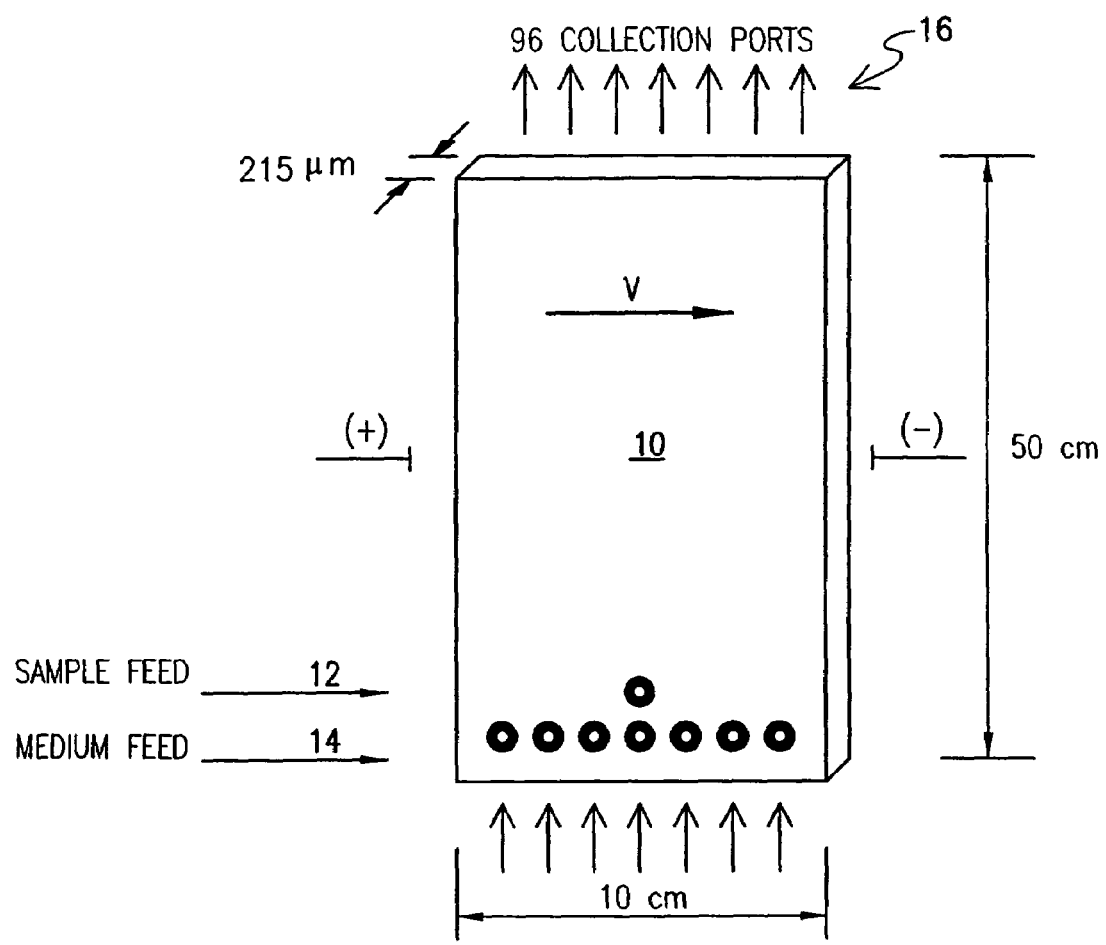
FIG. 1 is a schematic of the Octopus continuous free-flow electrophoretic system.

A method for altering the composition of a feed solution containing at least two components is provided. The feed solution is placed in a separation medium-filled separation chamber of an electrophoretic apparatus and an electrical potential is applied to the electrophoretic apparatus. The separation medium contains a resolving agent that differentially interacts with the components to cause migration of the bands of the component away from each other so as to separate the bands.

DESCRIPTION OF PREFERRED EMBODIMENTS

The approach of this invention is based on the principle that the number of cascade stages required to effect a binary separation decreases very rapidly as the value of separation selectivity increases. Applied to electrophoretic enantiomer separations this means that if one can force the band of one of the enantiomers to migrate cationically and the other anionically, both enantiomers will migrate away, in the opposite direction, from their feed position and separation can be achieved by migration through the shortest possible distance, the sum of the two band widths. According to the predictions of the charged resolving agent migration model (CHARM model) of electrophoretic enantiomer separations [B. A. Williams and G. Vigh, J. Chromatogr., 1997, 777, 295–309], one might be able to create such a situation by using a multiply charged anionic resolving agent (such as the single-isomer heptakis-6-sulfo-β-cyclodextrin) for the separation of the enantiomers of a single-charged cation (such as protonated terbutaline) in a unit such as the Octopus unit.

The CHARM model, which in a first approximation neglects the ionic strength effects, predicts that when a single-charged cationic enantiomer (either a strong base or a protonated weak base) is complexed with a single-isomer, multiply-charged anionic resolving agent, the effective electrophoretic mobility of the R enantiomer ($\mu^{eff}_R$) is $$\mu^{eff}_R = \frac{\mu^0 + \mu^0_{RCD}[CD]}{1 + K_{RCD}[CD]} \quad \text{(Eq. 1)}$$

and separation selectivity ($\alpha = \mu^{eff}_R/\mu^{eff}_S$) for the enantiomer pair is $$\alpha = \frac{\mu^0 + \mu^0_{RCD}K_{RCD}[CD]}{\mu^0 + \mu^0_{SCD}K_{SCD}[CD]} \frac{1 + K_{SCD}[CD]}{1 + K_{RCD}[CD]} \quad \text{(Eq. 2)}$$

where $\mu^0$, $\mu^0_{RCD}$, and $\mu^0_{SCD}$ are the ionic mobilities of the free and complexed enantiomers, $K_{RCD}$ and $K_{SCD}$ are the respective binding constants of the enantiomers, and [CD] is the species concentration of the free resolving agent. Eq. 1 predicts that the initially high cationic effective mobilities of the enantiomers decrease toward zero then, for sufficiently strongly binding enantiomers, become anionic as the concentration of the anionic resolving agent is increased. When the binding constants of the two enantiomers and/or the ionic mobilities of the two diastereomeric analyte-resolving agent complexes or both are different from each other, the resolving agent concentrations where the effective mobilities of the enantiomers change from cationic to anionic will be different for the two enantiomers. Consequently, there will be a resolving agent concentration at which the band of one of the enantiomers will still migrate cationically, while the band of the other enantiomer will already migrate anionically, and the absolute values of their effective mobilities will be equal. This migration behavior has been verified experimentally and has been exploited for the analytical-scale separation of weak base pharmaceuticals with several single-isomer, heptasulfated and octasulfated β- and Γ-cyclodextrins as the resolving agents [Tacker et al., Electrophoresis 1999, 20, 2794–2798].

This migration behavior allows one to propose a continuous, preparative-scale electrophoretic separation scheme for charged (both strong and weak electrolyte) enantiomers by (i) continuously feeding the separation chamber of an electrophoretic separator (or a portion thereof) with a separation medium in which $|\mu^{eff}_R|$ is approximately equal or equal to $|\mu^{eff}_S|$ and $\mu^{eff}_R/\mu^{eff}_S<0$, (ii) continuously feeding the mixture of the enantiomers into the section of the electrophoretic separator that contains such a separation medium, (iii) applying an electric potential orthogonal to the flow direction of the separation medium and (iv) continuously collecting the pure enantiomers at the downstream end of the separation chamber. This way, the enantiomers would have to migrate maximally only as much as the sum of the band widths, yet would become clearly separated from each other. Also, the total width of the separation chamber can be much smaller than what would be needed to achieve separation of the enantiomers when both of them migrate cationically or anionically.

Phosphoric acid, lithium hydroxide, 2-propanol (IPA) and hydroxypropylmethyl-cellulose (HPMC, average molecular weight 86,000) were obtained from Aldrich (Milwaukee, Wis.), β-alanine from Sigma (St. Louis, Mo.) and heptakis-6-sulfo-β-cyclodextrin (HS) was synthesized as described in Vincent, et al., Anal. Chem., 1997, 69, 4419–4428. All solutions were freshly prepared using deionized water from a Millipore Q unit (Millipore, Milford, Mass.).

The final separation medium used in the preparative-scale enantiomer separations contained 0.2% w/w HPMC, 12.5% v/v IPA, 50 mM β-alanine and 30 mM HS. The counter-flow solution at the outlet of the Octopus unit was 0.2% HPMC in de-ionized water. The sample was 5 mM racemic terbutaline and it was dissolved in the separation medium. The highly conductive anolyte and catholyte solutions were made by adding 50 mmol β-alanine, 75 mmol methanesulfonic acid and 75 mmol sodium hydroxide to 1 L deionized water.

The background electrolyte (BE) used for the capillary electrophoretic CE purity analysis of the collected fractions was made by adding 10 mmol HS to a 1 L volumetric flask and filling it to the mark with a stock solution of 25 mM $H_3PO_4$ titrated to pH 2.5 with LiOH.

The analytical-scale CE separations were completed on a P/ACE 5510 CE unit (Beckman-Coulter Instruments, Fullerton, Calif.). Its UV detector was operated at 214 nm. All CE separations were carried out in $L_d$=19 cm, $L_t$=26 cm, 25 μm I.D., 150 μm O.D. uncoated fused silica capillaries (Polymicro Technologies, Phoenix, Ariz.) at 10 kV. The cartridge coolant of the P/ACE was thermostated at 25° C.

All preparative-scale enantiomer separations were completed in the Octopus continuous free-flow electrophoretic unit (Dr. Weber GmbH, Kirchheim-Heimstetten, Germany). The schematic of the unit is shown in FIG. 1. The chamber coolant was thermostated at 10° C. The Octopus unit has a pair of anolyte recirculating ports (not shown in FIG. 1), a pair of catholyte recirculating ports (not shown), seven separation medium feed ports 14, central sample feed port 12, and a counter-flow feed port (not shown) at the top of the chamber above the 96 collection ports 16. Alternatively, sample feed port 12 may be omitted and a sample may be injected into chamber 10 through at least one of separation medium feed ports 14. A multichannel peristaltic pump (not shown) was used to feed all solutions to the ports. The separated fractions were collected through ninety six sample collection ports 16 at the exit end of the separation chamber, offering a lateral resolution of 1.04 mm/collection port. A 215 μm-thick zone electrophoresis separation chamber gasket was used in each experiment to form chamber 10.

The effective mobilities of the enantiomers were determined by conventional CE measurements as described in Vincent et al., Anal. Chem., 1997, 69, 4419–4428. The preparative, continuous free-flow enantiomer separations were completed by first filling the Octopus separation chamber with deionized water and removing all air. The separation medium was introduced through the inlet ports at a total flow rate of 35.0 mL/h. The sample was introduced through the central sample port at a rate of 2.5 mL/h. The counter-flow was pumped at 90.0 mL/h. Once stable flows were established, a separation potential of 350 V was applied across the 10 cm wide separation chamber. Fractions of 1.63 mL each were then collected in deep, 96-well titer plates and analyzed by CE for enantiomeric purity.

Figure 2:
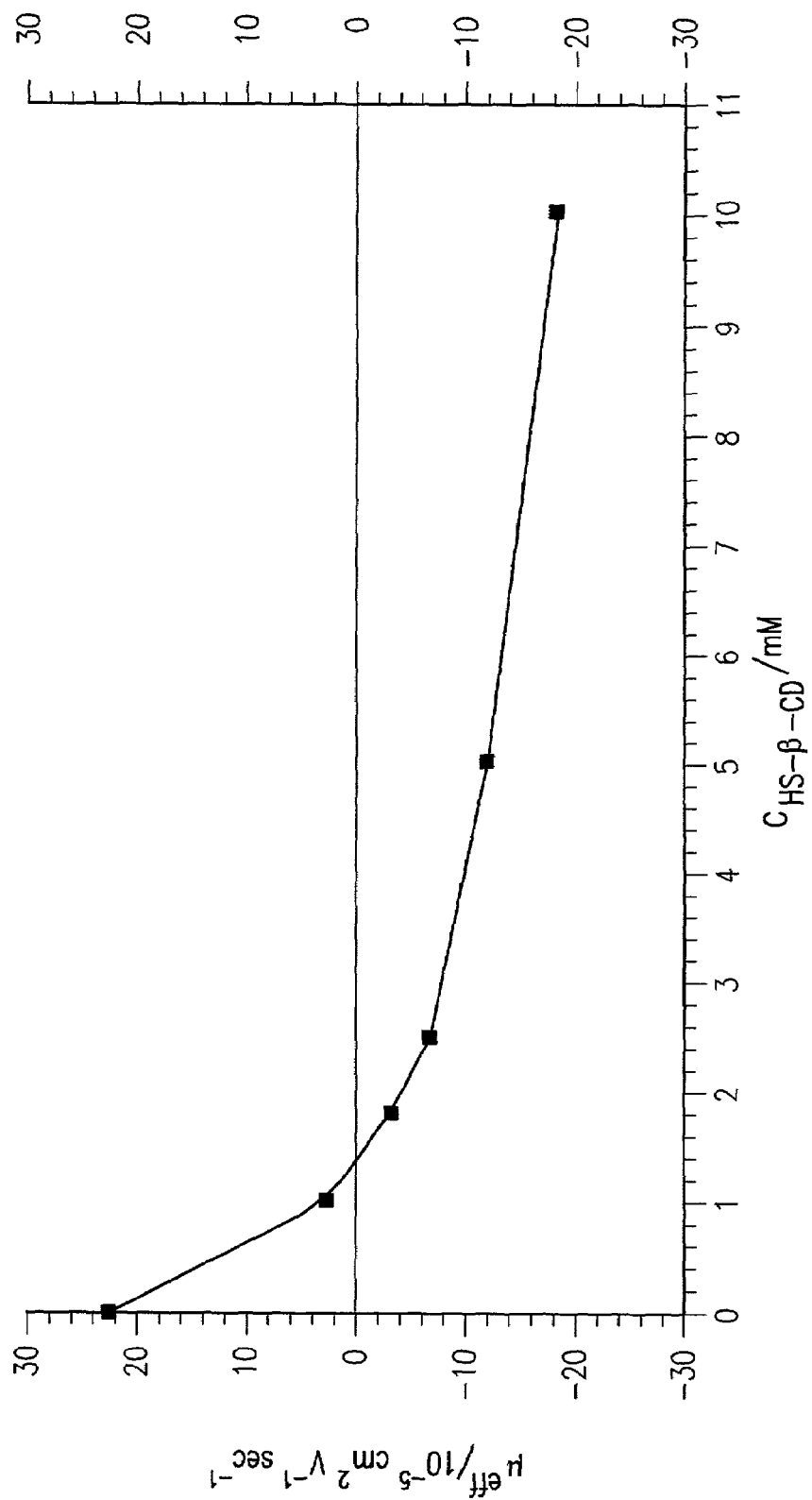
FIG. 2 shows the effective mobility ($\mu^{\textit{eff}}$) of the more strongly complexing terbutaline enantiomer as a function of the heptakis-6-sulfo-β-cyclodextrin (HS) concentration of the separation medium.
Figure 3:
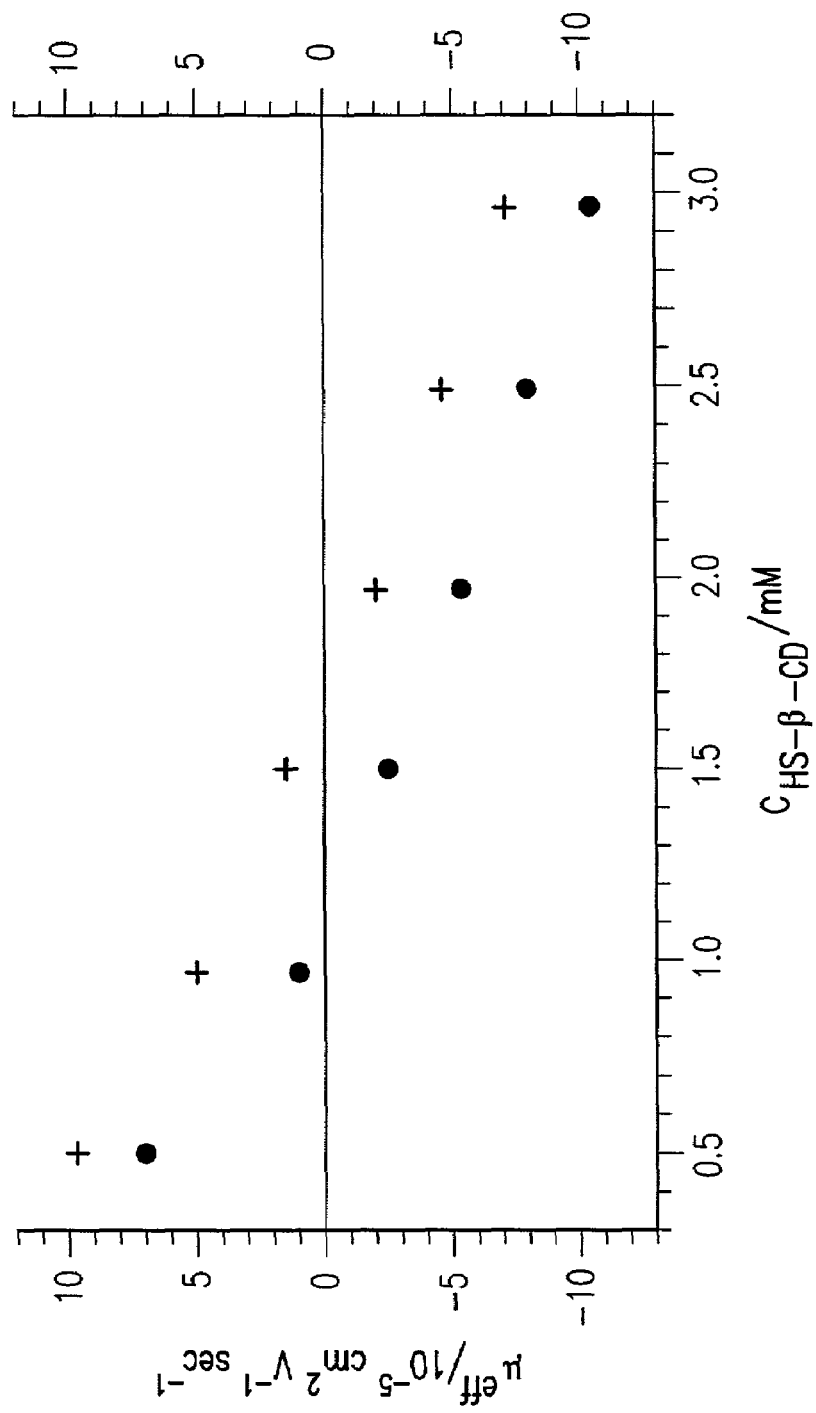
FIG. 3 shows the effective mobilities ($\mu^{\textit{eff}}$) of the less strongly binding (symbol: +) and more strongly binding (symbol: filled circle) terbutaline enantiomers as a function of the HS concentration of the separation medium around the cross-over point of the effective mobilities.

First, the effective mobilities of the terbutaline enantiomers were determined by CE at 25° C., as described in Vincent et al., Anal. Chem., 1997, 69, 4419–4428, by adding increasingly higher amounts of HS to a 25 mM $H_3PO_4$ solution that was adjusted to pH 2.5 with LiOH. The effective mobility of the enantiomer that had a lower cationic mobility in the 0.5 mM HS BE is shown in FIG. 2 for the entire HS concentration range studied. As predicted by the CHARM model, the initially cationic effective mobilities decrease, go through zero, and become increasingly anionic as the concentration of HS is increased. Since the effective mobility cross-over occurred between 1 and 2 mM HS concentration, the measurements were repeated, as shown in FIG. 3, with small increments in the 0.5 to 3 mM HS concentration range. The effective mobilities of the two enantiomers are equal in magnitude, but opposite in sign when the HS concentration is about 1.45 mM. Thus, this BE could be used for the proposed preparative separation scheme, except that (i) the sample load would have to be kept low, in line with the low HS concentration at which the mobility cross-over occurs, and (ii) the conductivity of the acidic buffer (11.6 mScm$^{-1}$) would be prohibitively high for the Octopus unit.

Figure 4:
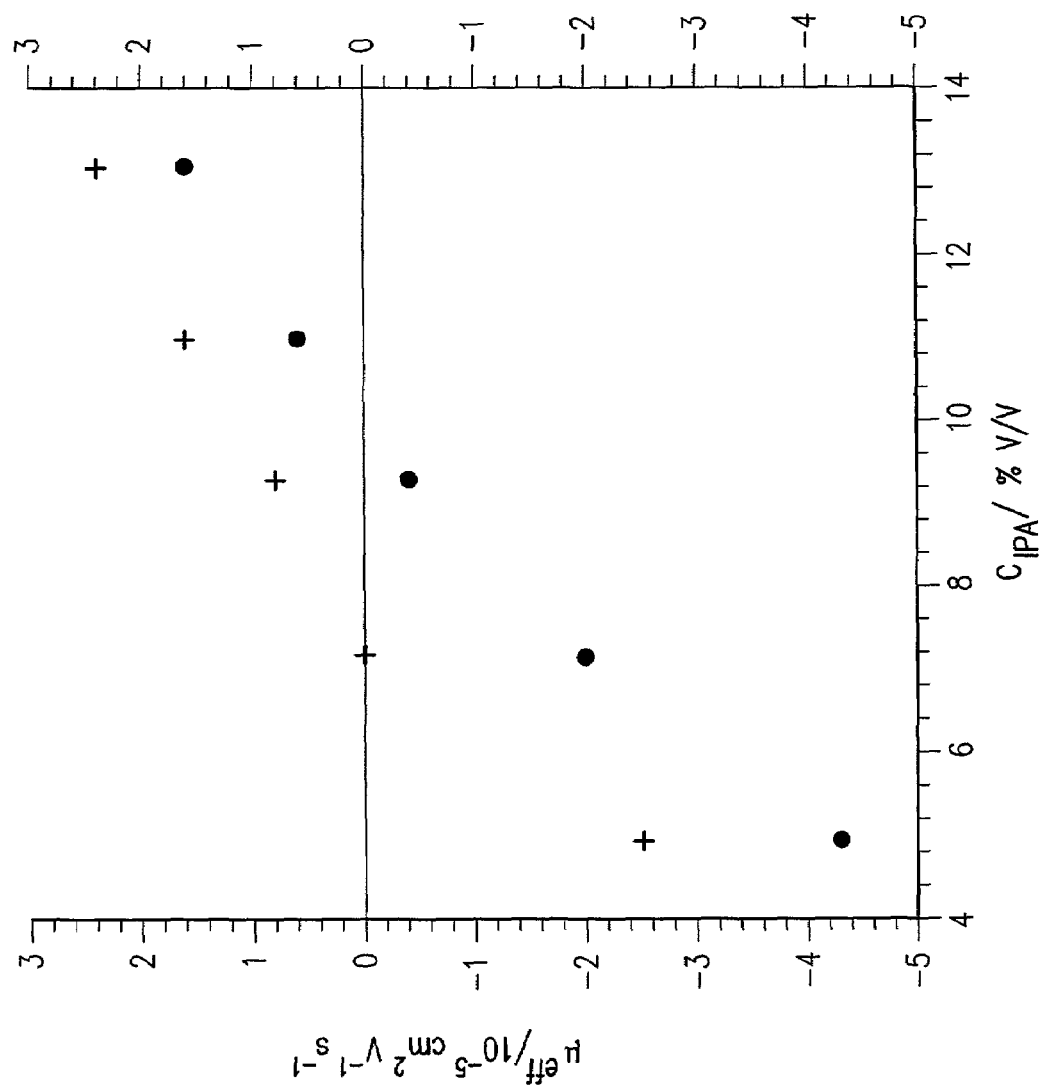
FIG. 4 shows the effective mobilities ($\mu^{\textit{eff}}$) of the less strongly binding (symbol: +) and more strongly binding (symbol: filled circle) terbutaline enantiomers as a function of the isopropanol (IPA) concentration in a 30 mM HS separation medium.
Figure 5:
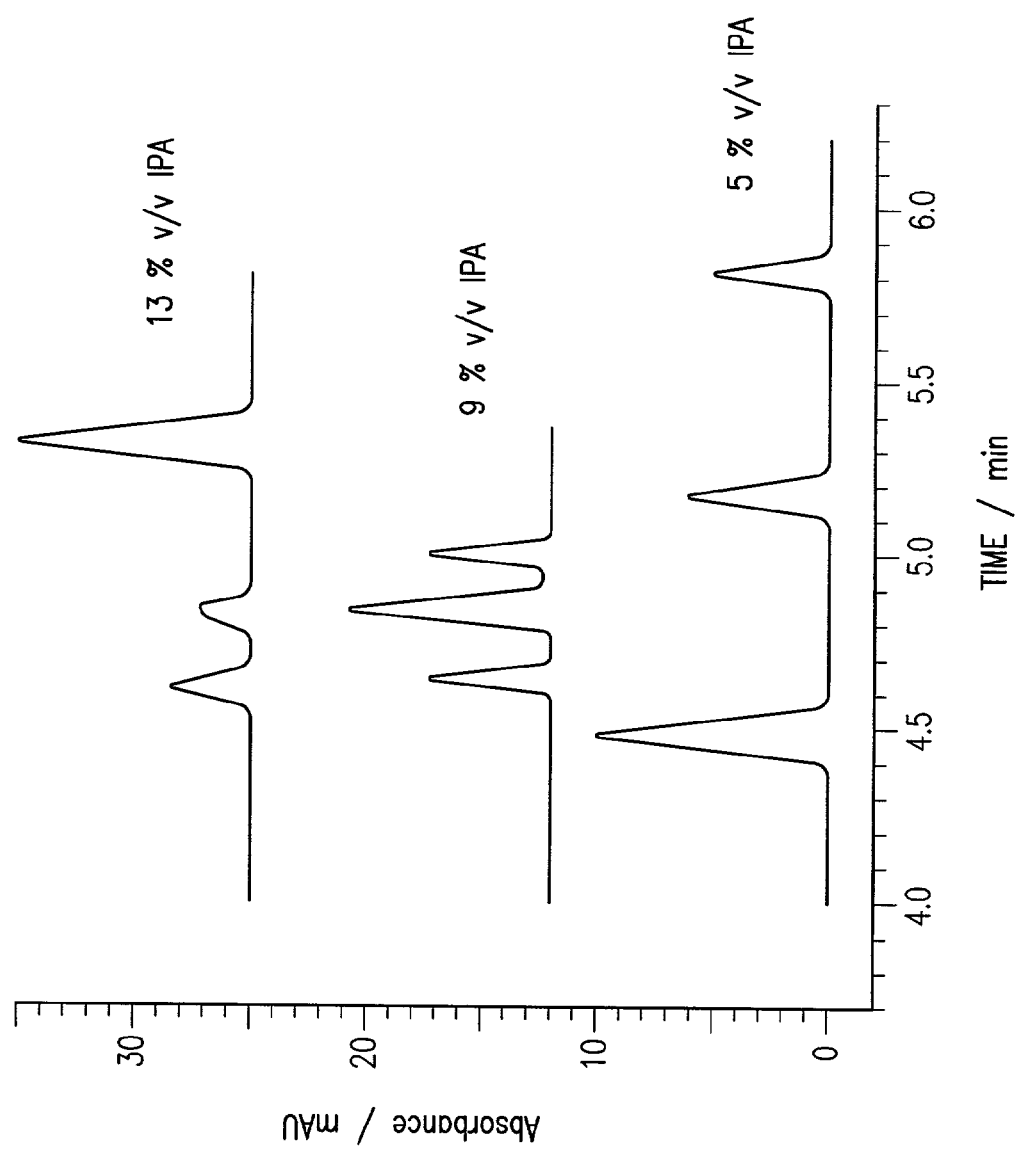
FIG. 5 shows the electropherograms of the terbutaline enantiomers (small peaks) and nitromethane (tall peaks) in the 30 mM HS, 5% v/v IPA separation medium (bottom trace), 30 mM HS, 9% v/v IPA separation medium (middle trace), and 30 mM HS, 13% v/v IPA separation medium (top trace).

Therefore, a second BE containing 50 mM β-alanine and 30 mM HS (pH 6.04) was prepared and the effective mobilities of the terbutaline enantiomers were again measured at 25° C. As expected, strongly anionic effective mobilities were observed. Next, increasing amounts of isopropanol (IPA) were added to this stock BE and the effective mobilities were re-measured as shown in FIG. 4. The extent of complexation between HS and the terbutaline enantiomers decreased as the concentration of IPA was increased. Complexation became so weak above an IPA concentration of 11% v/v that the effective mobilities of both enantiomers became cationic. Thus, by adding enough IPA to the BE, effective mobilities similar to those around the mobility cross-over point in FIG. 3 could be obtained with HS concentrations as high 30 mM. The electropherograms containing the terbutaline enantiomers and nitromethane (a very weakly bound neutral marker) in three different BEs are shown in FIG. 5. In each electropherogram, the two small peaks correspond to the terbutaline enantiomers, the tall peak to nitromethane. Clearly, the bands of both enantiomers migrate cationically in the BE that contains 13% v/v IPA. The enantiomer bands are spaced about evenly on the cationic and anionic sides of nitromethane when there is 9% v/v IPA in the BE. The bands of both enantiomers migrate anionically when the IPA concentration is 5% v/v. These electropherograms indicate that the proposed preparative separation scheme is feasible.

Figure 6:
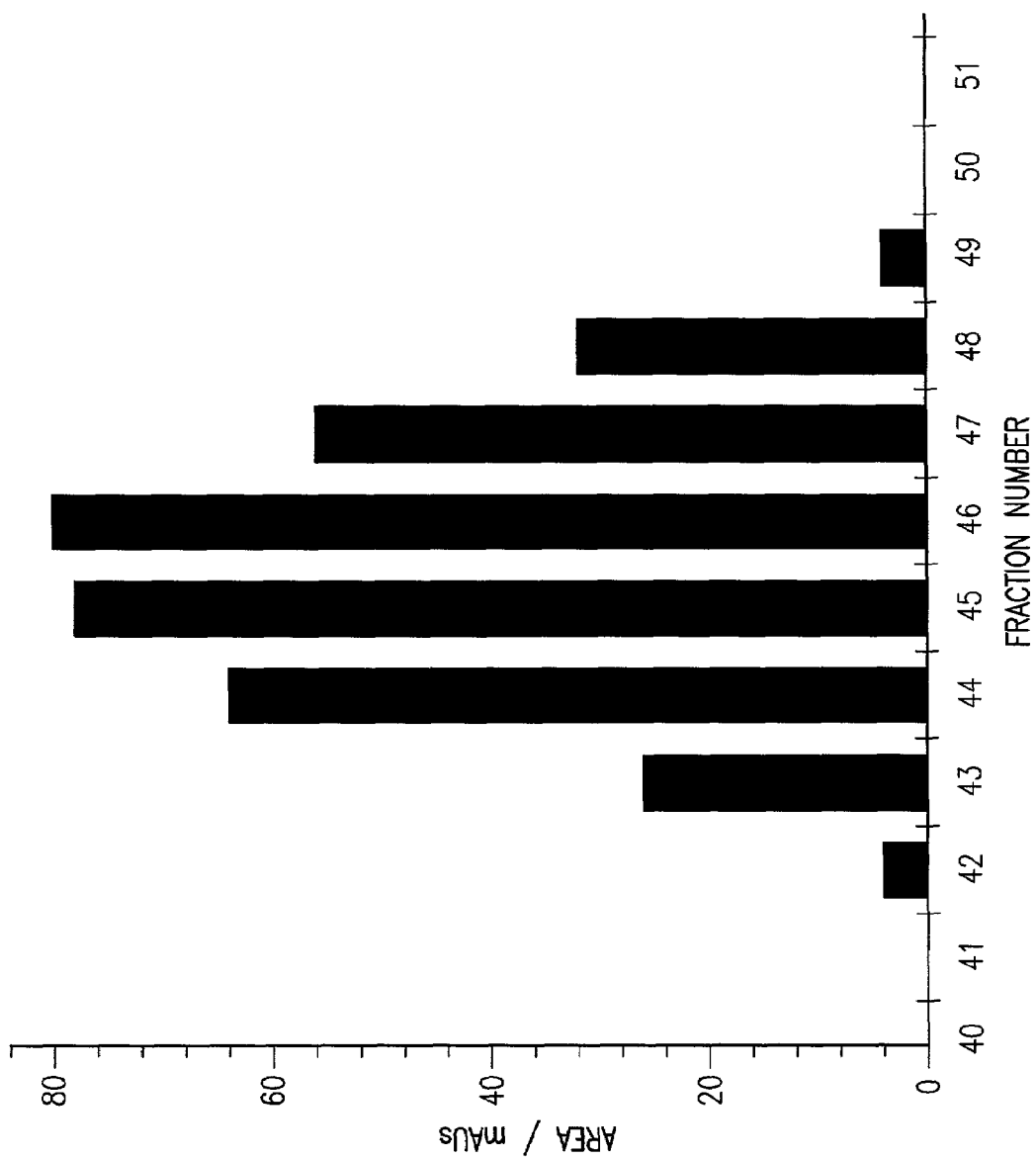
FIG. 6 shows the distribution of terbutaline in the fractions collected at the exit of the Octopus unit; hydrodynamic flow only, no electrophoresis.

The Octopus unit has to be operated at or below 10° C. so as not to overheat (and damage) its PLEXIGLAS top plate. Since the P/ACE unit that was available for the mobility measurements cannot reach such a low temperature, the IPA concentration at which equal-but-opposite enantiomer mobilities occur in the 30 mM HS separation medium (see above) had to be adjusted slightly, as follows. First, one can determine the actual fraction number in the Octopus that corresponds to the sample feed position by continuously injecting the racemic terbutaline feed stream, without turning on the separation potential, and determining the concentration distribution of terbutaline in the collected fractions. The centroid of the terbutaline band indicates the feed position in terms of fraction numbers. As shown in FIG. 6, our feed band centroid was at fraction 46 and the band was eight fractions wide. Next, one can repeat the same experiment, but with the separation potential turned on, and look for the change in the concentration distribution of terbutaline in the collected fractions. The IPA concentration at which the spread remains symmetric around the original centroid position (in our case, fraction 46), indicates the point where the enantiomers have equal-but-opposite mobilities. In our case, this IPA concentration was 12.5% v/v. The conductivity of this separation buffer at 10° C. was 7 mScm$^{-1}$, a more favorable value than that of the phosphoric acid-based separation buffer.

Figure 7:
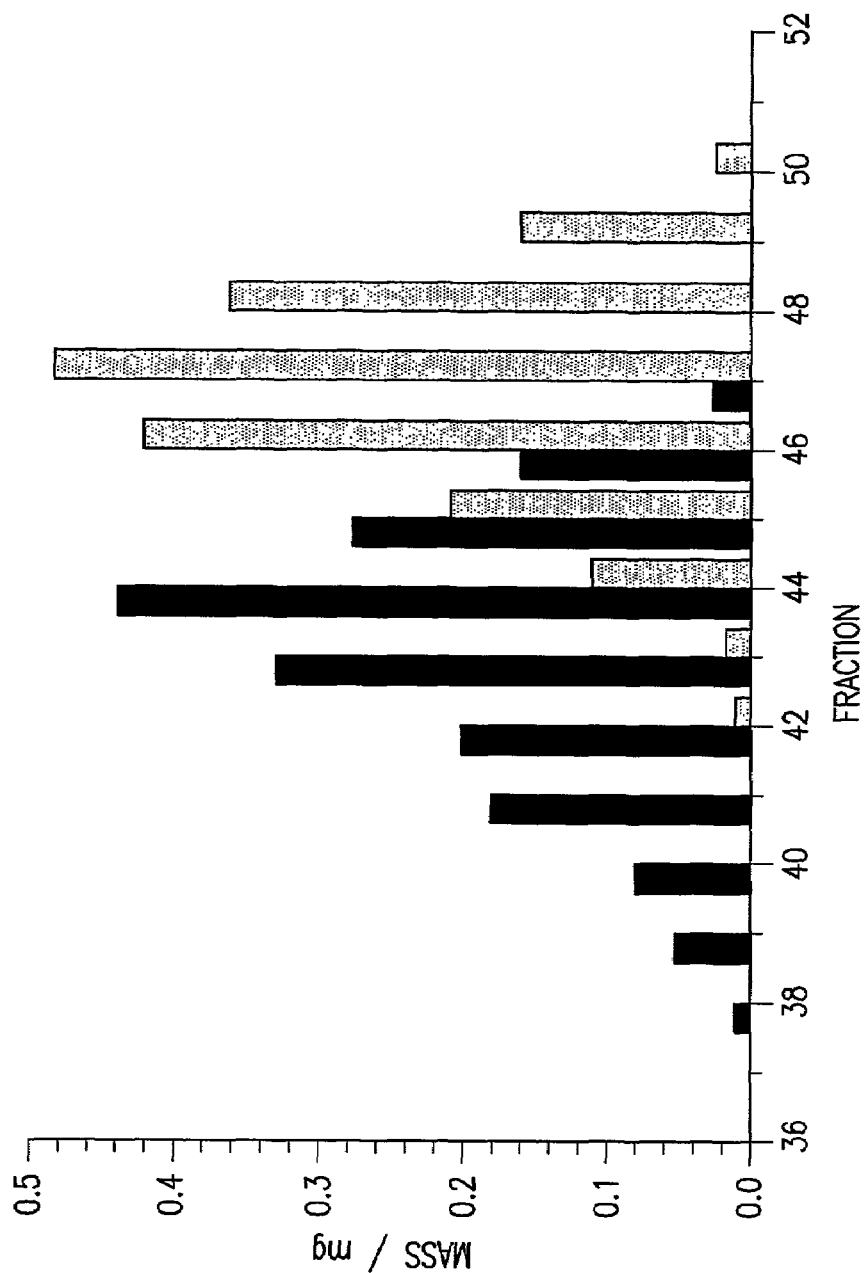
FIG. 7 shows the distribution of terbutaline enantiomers in the fractions collected at the exit of the Octopus unit after electrophoresis. Solid black columns: less strongly binding enantiomer with cationic effective mobility. Hatched columns: more strongly binding enantiomer with anionic effective mobility.

The results of a 1.25 hour long preparative run are shown in FIG. 7. The collected fractions were analyzed by CE to determine the amounts of the terbutaline enantiomers in each fraction. The concentration distribution obtained is plotted in FIG. 7. The concentration maxima of the two enantiomer bands are separated from each other by about three fractions. Each enantiomer band is only ten fractions wide, which means that the width of the electrophoresed band increased only by about 20% over that of the non-electrophoresed band (compare FIGS. 6 and 7). This represents a significant improvement in band width compared to what was observed either in intermittent-flow mode zone electrophoretic separation of enantiomers (a band width of twenty fractions, see FIG. 7 in Hoffman et al., Anal. Chem., 1999, 71, 1840–1850) or the continuous flow mode zone electrophoretic separation of enantiomers (a band width of forty fractions, see FIG. 6 in the same paper). We believe that the main reason for the significantly improved band width is the fact that when the equal-but-opposite analyte mobility principle disclosed here is utilized, the bands do not have to travel across such a long section of the separation chamber as when they both migrate cationically or anionically and experience all the undesirable distortion effects such as discussed in Rhodes et al., App. Theor. Electrophor. 1991, 2, 87–98.

Figure 8:
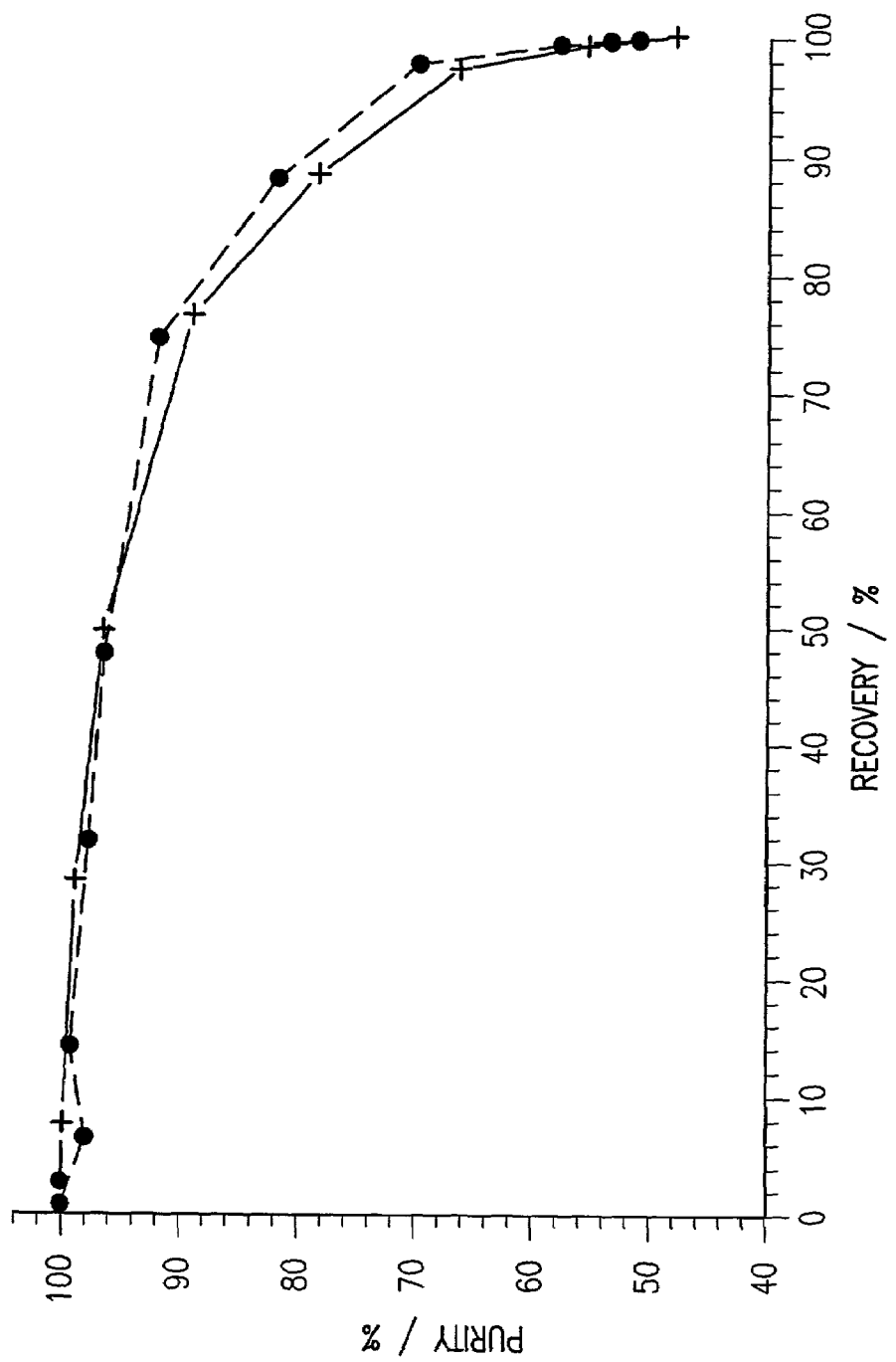
FIG. 8 shows the cumulative purity vs. % recovery curves for the continuous free-flow electrophoretic separation shown in FIG. 7. Symbol +: less strongly binding enantiomer with cationic effective mobility. Symbol circle: more strongly binding enantiomer with anionic effective mobility.

Purity vs. cumulative recovery curves are calculated by pooling the fractions from the opposite sides of the enantiomer bands (e.g., beginning to pool from fraction 36 toward 48 for one of the enantiomers and from fraction 52 toward 40 for the other enantiomer in FIG. 7). These purity vs. cumulative recovery curves are shown in FIG. 8. The curves indicate that about 50% of both enantiomers can be recovered with a purity of better than 97%, or 90% of each enantiomer can be recovered with a purity of better than 80%.

One of the greatest advantages of the proposed preparative continuous free-flow electrophoretic separation scheme described here is that when the anionic and cationic effective mobilities of the enantiomer bands are equal in magnitude but opposite in sign, the two enantiomers will migrate away from each other, in opposite direction. Thus, in principle, a separation channel as narrow as a few times the width of the sample feed stream is all that is required to achieve the separation. Consequently, the potential applied across the separation channel can be very low, even at reasonably high field strength values. This scheme is radically different from the regular free-solution preparative electrophoretic separation systems where a significant migration distance must be covered before the two enantiomers pull away from each other. In other words, by operating around the zero mobility point, the common, non-separative part of the effective mobilities of the enantiomers can be eliminated and the useful, separative $\Delta\mu^{eff}$ part retained.

Special free-flow electrophoretic systems, designed around this single-stage, binary separation principle, can be used to achieve the facile electrophoretic separation of weak or strong electrolyte enantiomers. In addition, the same principle can also be used for the preparative-scale separation of any other, nonchiral analyte pair (a pair of ionic analytes, or a pair consisting of one neutral and one ionic analyte), as long as an interacting agent having greater and opposite charge than the analyte and capable of bringing about opposite analyte mobilities is used.

In general, when one of the components of the feed solution is entity A, and the other component is entity B, which interact with resolving agent R according to equilibrium reactions $A+R \leftrightarrow AR$ and $B+R \leftrightarrow BR$, the effective electrophoretic mobilities of the bands of the two components, $\mu^{eff}_A$ and $\mu^{eff}_B$, are $$\mu^{eff}_A = \frac{\mu^0_A + \mu^0_{AR}[R]}{1 + K_{AR}[R]} \quad \text{(Eq. 3)}$$

and $$\mu^{eff}_B = \frac{\mu^0_B + \mu^0_{BR}[R]}{1 + K_{BR}[R]} \quad \text{(Eq. 4)}$$

and separation selectivity ($\alpha = \mu^{eff}_A / \mu^{eff}_B$) for the enantiomer pair is $$\alpha = \frac{\mu^0_A + \mu^0_{AR}K_{AR}[R]}{\mu^0_B + \mu^0_{BR}K_{BR}[R]} \frac{1 + K_{BR}[R]}{1 + K_{AR}[R]} \quad \text{(Eq. 5)}$$

where $\mu^0_A$, $\mu^0_B$, $\mu^0_{AR}$, and $\mu^0_{BR}$ are the ionic mobilities of entities A, B, AR and BR, $K_{AR}$ and $K_{BR}$ are the respective equilibrium coefficients characterizing the interactions of entities A and R in forming entity AR and B and R in forming entity BR, and [R] is the species concentration of the free resolving agent R. When separation selectivity, $\alpha$ is less than zero, the bands of A and B migrate away from each other in opposite direction, when the value of $\alpha$ is equal to zero, the band of A or B migrate away from the other band that has zero effective mobility. Thus, the bands can be separated from each other by migrating a distance as short as the sum of the band widths (when $\alpha=0$) or the sum of the two half widths (when $\alpha<0$).

If the analyte is a chiral compound, i.e., if the analytes are a pair of enantiomers, then the resolving agent has to be an enantiomer that interacts with the two analyte enantiomers differently. If the analytes are two different proteins, then the resolving agent has to be a compound that binds to those two proteins differently. Any compound that interacts with an analyte and changes the sign of its effective mobility can act as a resolving agent for the analyte. There is a complementarity between the analyte and its resolving agent. One can select analyte and resolving agent pairs either based on available complexation data, separation data, or one can select them by experimentation.

Preferably, the electrical conductivity of the separation medium in the separation chamber is low to minimize excess heat production. Preferably, the composition of the separation medium is selected to minimize electromigration dispersion of the analyte bands.

The analytes are caused to move in opposite directions according to the methods of this invention. In a preferred embodiment the mobilities in opposite directions are equal. In another embodiment the movement of analytes is in opposite directions and the absolute values of their mobilities are different. In yet another embodiment the band of one of the analytes does not move while the other band moves.

Compounds such as isopropanol may be used as a "competing agent" to affect the chemical equilibrium constant between the resolving agent and an analyte. Other well known solvents or competing compounds may also be used.

By using this invention, fast, efficient, preparative-scale electrophoretic separations can be obtained for weak or strong electrolyte analytes that have very similar effective mobilities, because the analytes have to migrate only a distance that is equal to the sum of the respective band widths. The principle opens an entirely new application field for preparative-scale electrophoretic separations. Multiple units can be operated in parallel to scale the method and apparatus to a desired capacity for separations. In a preferred embodiment, the width of the separation channel is barely wider than the sum total of the two band widths of the analytes.

While particular embodiments of the present invention have been shown and described, it will be obvious to those skilled in the art that changes and modifications may be made without departing from the invention in its broader aspects. The scope of the invention is intended to be defined in the following claims when viewed in their proper perspective.

What is claimed is:

1. A method for electrophoretically altering the initial composition of a feed solution containing at least two components, entities A and B, comprising:

providing an electrophoretic apparatus having a separation chamber and a pair of electrodes;

providing a separation medium containing a selected resolving agent R at a selected concentration [R] to cause the bands of entities A and B to have an effective electrophoretic mobility $\mu^{\textit{eff}}_A$ and $\mu^{\textit{eff}}_B$ and separation selectivity, $\alpha$, where $$\mu^{\textit{eff}}_A = \frac{\mu^0_A + \mu^0_{AR}[R]}{1 + K_{AR}[R]}$$

and $$\mu^{\textit{eff}}_B = \frac{\mu^0_B + \mu^0_{BR}[R]}{1 + K_{BR}[R]}$$

$$\alpha = \frac{\mu^{\textit{eff}}_A}{\mu^{\textit{eff}}_B} = \frac{\mu^0_A + \mu^0_{AR} K_{AR}[R]}{\mu^0_B + \mu^0_{BR} K_{BR}[R]} \frac{1 + K_{BR}[R]}{1 + K_{AR}[R]}$$

and $\mu^0_A$, $\mu^0_B$, $\mu^0_{AR}$, and $\mu^0_{BR}$ are the ionic mobilities of entities A, B, AR and BR, $K_{AR}$ and $K_{BR}$ are the respective equilibrium coefficients characterizing the interactions of entities A and R in forming entity AR and B and R in forming entity BR, and [R] is the species concentration of the free resolving agent R, wherein when at least one of $\mu^0_A$ or $\mu^0_B$ is not equal to zero, the selected resolving agent R is selected to cause at least one of the ratios $\mu^0_A/\mu^0_{AR}$ or $\mu^0_B/\mu^0_{BR}$ to be less than or equal to zero, and [R] is selected to cause $\alpha$ to be less than or equal to zero;

applying an electric potential between the pair of electrodes; and collecting a desired fraction from the eletrophoretic apparatus;

wherein the effective electrophoretic mobility of the bands of entities A and B are equal in magnitude and opposite in sign.

2. The method of claim 1 wherein the electrophoretic apparatus is a continuous free-flow electrophoretic apparatus.

3. The method of claim 1 wherein at least one of entities A or B is a weak or a strong electrolyte.

4. The method of claim 1 wherein entities A and B are enantiomers.

5. The method of claim 1 wherein the species concentration of the free resolving agent R in the separation medium is altered to alter the value of $\alpha$.

6. The method of claim 1 wherein an additional component is added to the separation medium to alter the value of $\alpha$.

7. The method according to claim 6 wherein the additional component is a solvent.

8. The method according to claim 6 wherein the solvent is isopropanol.

9. The method according to claim 6 wherein the additional component competes with at least one of entity A or B for resolving agent R.

10. The method of claim 1 wherein the selected resolving agent is a charged cyclodextrin.

11. The method of claim 1 wherein the selected resolving agent is a single isomer charged cyclodextrin.

12. The method of claim 1 wherein the selected resolving agent is a mixture of cyclodextrins.

13. The method of claim 1 wherein a plurality of separation chambers is provided.

14. A method for electrophoretically altering the initial composition of a feed solution containing at least a component A and a component B, comprising:

providing an electrophoretic apparatus having a separation chamber and a pair of electrodes;

providing a separation medium containing a selected resolving agent at a selected concentration to cause a band of component A and a band of component B to be separated around a zero effective mobility point of the band of component A and component B by operation of the electrophoretic apparatus; and collecting a desired fraction from the electrophoretic apparatus;

wherein the band of component A and the band of component B is separated at an equal effective mobility around the zero effective mobility point.

15. The method of claim 14 wherein the equal effective mobility is altered by an addition of a competing agent.

16. The method of claim 14 wherein the components A and B are enantiomers.

17. The method of claim 14 wherein the resolving agent is a charged chiral resolving agent.

18. The method of claim 17 wherein the charged chiral resolving agent is a charged cyclodextrin.

* * * * *